United States Patent [19]

Kervennal et al.

[11] Patent Number: 4,595,744

[45] Date of Patent: Jun. 17, 1986

[54] LOW MELTING POINT DIPHENYLETHANE DIISOCYANATE MIXTURES, METHOD OF MAKING THE SAME, AND POLYURETHANES MADE THEREFROM

[75] Inventors: Jacques Kervennal, Lyons; Henri Mathais, St-Didier-au-Mont-d'Or, both of France

[73] Assignee: Atochem, France

[21] Appl. No.: 679,571

[22] Filed: Dec. 7, 1984

[30] Foreign Application Priority Data

Dec. 21, 1983 [FR] France .................................. 83 20458

[51] Int. Cl.$^4$ .............................................. C08G 18/76
[52] U.S. Cl. ........................................ 528/83; 528/85; 560/359; 560/347
[58] Field of Search .................. 260/453 PH, 453 AR; 528/83, 85

[56] References Cited

U.S. PATENT DOCUMENTS 4,193,932  3/1980  Yamamoto et al. ......... 260/453 PH

*Primary Examiner*—Maurice J. Welsh
*Attorney, Agent, or Firm*—Sigalos & Levine

[57] ABSTRACT

Low melting point compositions, comprising a mixture of diisocyanate isomers having the diphenylethane structure, and containing by weight about:

35 to 55% of 2,4' isomer,
15 to 40% of 4,4' isomer,
10 to 25% of 2,2' isomer,
3 to 10% of 3,4' isomer, and
3 to 8% of 2,3' isomer;

to the method of making such compositions by the nitration of aromatic diphenylethane rings, followed by a hydrogenation and phosgenation; and polyurethanes formed utilizing such compositions.

5 Claims, No Drawings

LOW MELTING POINT DIPHENYLETHANE DIISOCYANATE MIXTURES, METHOD OF MAKING THE SAME, AND POLYURETHANES MADE THEREFROM

BACKGROUND OF THE INVENTION

The invention concerns new compositions of isocyanates containing diisocyanates having a diphenylethane structure and obtained from diphenylethane by the dinitration of aromatic rings, followed by a hydrogenation and a phosgenation. The compositions possess a lowered melting point as compared to the diisocyanates of dibenzyl already known in the literature; in addition they have the property of remaining fluid for several hours, which facilitates their use, especially in the production of polyurethanes. The distribution by weight of the diisocyanates in this composition amounts to 35 to 55% of the 2,4' isomer, 15 to 40% of the 4,4' isomer, 10 to 25% of the 2,2' isomer, 3 to 10% of the 3,4' isomer, and 3 to 8% of the 2,3' isomer.

Diisocyanates of diphenylmethane aromatic hydrocarbon structure are synthesized industrially (M.D.I.). They are obtained by the condensation of two molecules of aniline on one molecule of formaldehyde in the presence of an acid catalyst, followed by a phosgenation, leading to mixtures containing the 4,4', 2,4', and 2,2' isomers. But this condensation is never totally selective in 2-ring products and customarily mixtures of polyisocyanates and diisocyanates are synthesized, with the latter being separated by distillation in order to yield pure M.D.I. The 4,4' M.D.I. isomer is generally clearly predominant and possesses a melting point of 38° C. Thus, depending on its content, it can be necessary to liquefy the diisocyanate mixture before being able to use it, either by melting it and working in the hot state or by converting it chemically.

Isocyanates of diphenylethane structure have already been described in the literature; we are dealing with diphenylethane-4,4'-diisocyanates whose preparation by phosgenation of the corresponding diamine has been published by E. COCEA, A. CARACULACU, C. MARCULESCU, A. PETRUS, I. MATEI in Studii si Cercetàri Stiintifice-Chimie. Academia R. P. Române Filiala Iasi (1959), 10, no. 2, p. 261. The phosgenation has likewise been described in Japanese Pat. No. 41-6583. After distillation, there is thus obtained a diisocyanate having a melting point of 88°–89° C., which necessitates working at an elevated temperature in order to manufacture polyurethanes.

Some publications treat applications of this diisocyanate. I. MATEI, E. COCEA, A. CARACULACU, A. PETRUS in Studii si Cercetàri Stiintrifice-Chimie. Academia R. P. Române Filiala Iasi (1960), 379 and D. J. LYMAN, J. HELLER, M. BARLOW in Die Makromolekulare Chemie 84, p. 64 (1965) have described the synthesis and certain properties of polyurethanes derived from diphenylethane-4,4'-diisocyanate.

The diphenylethane-2,2'-diisocyanate has also been cited in French Pat. No. 1,492,642, but its melting point of 78°–79° C. is likewise elevated. In can be prepared by oxidizing duplication of orthonitrotoluene, followed by a hydrogenation and then a phosgenation; however, the yield from the first stage is mediocre.

If the oxidizing duplication is carried out starting from a mixture of the isomers of nitrotoluene, then a mixture of dinitro isomers is obtained which it is possible to hydrogenate and phosgenate. But there again, the yield from the first stage is mediocre and it is the 4,4' isomer which is favored. There is thus obtained a mixture of diisocyanates in which this isomer predominates and which does not present the fluid properties of the compositions in conformity with the present invention.

SUMMARY OF THE INVENTION

The compositions in conformity with this invention have the advantage of having a lowered melting point as compared to the pure isomers cited precedingly. In addition, once melted, they present the particularity of remaining fluid for several hours, making it possible to use them in the liquid state, at ordinary temperature. Furthermore, the fact of obtaining mixtures of isomers makes it possible to have isocyanate groups of variable reactivities.

Briefly, the present invention comprises low melting point compositions comprising a mixture of diisocyanate isomers having a diphenylethane structure and containing by weight about:
- 35 to 55% of the 2,4' isomer,
- 15 to 40% of the 4,4' isomer,
- 10 to 25% of the 2,2' isomer,
- 3 to 10% of the 3,4' isomer, and
- 3 to 8% of the 2,3' isomer; and the method of making such compositions and polyurethanes made therefrom as set forth below.

DETAILED DESCRIPTION

The synthesis of the isocyanates according to the invention calls on three successive reaction stages starting with diphenylethane; one of nitration of the aromatic rings, one of hydrogenation, and one of phosgenation.

The diphenylethane used as raw material can be prepared by oxidizing duplication of toluene as described by K. H. D. LIU and Y. YAMASAKI in Bull. Jpn. Pet. Inst. (1976), 18, 45 or by condensation of the FRIEDEL-CRAFTS type of dichloroethane on benzene such as published by Y. SHUZO and H. TAKAO in J. Soc. Chem. Ind. Japan 47, 814 51944.

For the nitration one uses a mixture of nitric acid and sulfuric acid concentrated to at least 90% by weight; a lower concentration leads to a prohibitive formation of mononitro derivatives. The nitric acid can be used in stoichiometrical quantities with respect to the aromatic compound, thus using one mole of acid per aromatic ring to be nitrated. It is, however, advantageous to operate in the presence of a nitric acid excess which can go up to 20% with respect to the stoichiometric proportions. A greater excess would result in a prohibitive formation of trinitro derivatives. The sulfuric acid can be used in equimolar quantity with respect to the nitric acid, but it can be placed in excess or in a lesser amount. The nitration reaction can take place between 0° C. and the boiling temperature of the mixtures; usually between 0° C. and 50° C., with the aromatic compound preferably being rendered soluble in a solvent such a methylene chloride. The addition of the mixture of acids can thus be undertaken at 0° C., but it is not troublesome to operate at ambient temperature, on the condition of controlling the exothermicity of the reaction. The latter can proceed at ambient temperature, but it is preferable to operate with refluxing of the mixture, which permits partly eliminating the excess of nitric acid. The upper organic phase is then separated from the acids, neutralized and evaporated to dryness. It is recommended to operate under nitrogen atmosphere in a reactor equipped with means of efficient agitation and temperature control.

By following the operating method thus described, starting with pure diphenylethane, one obtains products formed essentially of dinitration isomers, containing from 35 to 55% of 2,4-dinitrodiphenylethane, from 15 to 40% of the 4,4' isomer, from 10 to 25% of the 2,2' isomer, from 3 to 10% of the 3,4' isomer, and from 3 to 8% of the 2,4' isomer.

The second stage constitutes the hydrogenation of the nitro derivatives into corresponding amines. It can be chemical but it is preferable to operate under hydrogen pressure in a reactor resistant to pressure, equipped with an agitation mechanism and possessing standard means for control and regulation, in the presence of a catalyst based on nickel, palladium, platinum, ruthenium, and others.

In this case, one uses a hydrogenation reactor making it possible to work under pressures which can attain 100 bars. The reaction can take place without solvent at a temperature at which the nitro derivative is melted, or in classical hydrogenation solvents such as alcohols, dioxane, ethylene glycol ethers, and others.

One preferably uses a catalyst constituted of palladium deposited on support at concentrations between 1 and 10%, which permits operating at temperatures between 30° and 100° C. and pressures from 20 to 50 bars. The molar ration of nitro derivatives/palladium is not imperatively fixed, but it is preferably between 200 and 3000. After reaction and filtration of the catalyst, the solvent, if used, is evaporated and the mixture of amines obtained can be used as is. It is also possible at this stage to separate the isomers of diamino-diphenylethane by distillation or by recrystallization.

The third stage uses standard phosgenation techniques in a reactor equipped with an agitation mechanism and topped by a refrigerant. For example, the mixture of amines is placed at a concentration of 5 to 20% into a chlorinated aromatic solvent such as monochlorobenzene or orthodichlorobenzene containing the required quantity of phosgene, while maintaining the temperature in the neighborhood of 20° C. The suspension is then heated progressively. The reaction mixture becomes homogenized at about 100° C. One continues to slowly raise the temperature to the boiling point of the mixture, then one distills the solvent so as to recover the isocyanates formed.

Another technique consists of introducing jointly into the reactor heated to above 80° C. a solution of the diamine isomers in the selected solvent and a stream of gaseous phosgene in slight excess. The formation of the isocyanates is then practically immediate.

One can also form the amine hydrochlorides in a first instance, then cause same to react with a stream of gaseous phosgene at a temperature above 120° C.

In all cases, the solvent is then distilled so as to recover the crude isocyanates formed. The latter can be used as is for instance in certain formulations of polyurethanes. However, the diisocyanate isomers can be distilled under a high vacuum so as to obtain the composition of the invention in pure form.

The invention will be further described in connection with the following examples which are set forth for purposes of illustration only.

Therein, the nitro derivatives have been analyzed by vapor phase gas chromatography by using a pyrex column having an internal and external diameters of 3 and 6 mm, respectively, and a length of 2 meters, filled with phase SP 2250 impregnated at 3% on 100–120 mesh Supelcoport support (SUPELCO) on which a linear temperature programming has been carried out at 40° C./min from 180° C. to 280° C. The principal dinitro isomers were synthesized pure or isolated by trapping and identified by nuclear magnetic resonance of $^{13}C$ and $^1H$.

For the amines, likewise analyzed by gas chromatography, one uses a 2-meter long glass column filled with 60–80 mesh W.N.A.W. chromosorb support (JOHNS MANVILLE), impregnated with 5% KOH and 5% apiezon N (Societe Apiezon Products Limited), by operating isothermally at 220° C. The concentrations in total amine functional groups are determined chemically. The NCO functional groups of the isocyanates are evaluated by chemical determination, whereas, the compositions in isomers are determined by gas chromatography on the column and under the conditions used for the nitro derivatives.

EXAMPLE 1

In a reactor of 6-liter capacity, 500 g of diphenylethane (2.74 moles) are dissolved in 1.1 liters of methylene chloride. A mixture of 387.5 g of 98.7% nitric acid (excess of 10% with respect to stoichiometrical proportions), and 750 g of 96% sulfuric acid (excess of 34%) is slowly introduced at ambient temperature. The addition requires 45 minutes and then the mixture is refluxed for 3½ hours. After cooling, 2.2 liters of methylene chloride are added and settling is allowed to take place. The organic phase is extracted with two complementary fractions of 1.5 l of methylene chloride, then neutralization is undertaken with the help of sodium carbonate and filtration. After evaporation of the solvent, one recovers 730 g of a solid white-yellow product melting at 140° C. The analysis of vapor phase gas chromatography yields the following proportions of isomers:

41.8% of the 2,4' isomers,
32.4% of the 4,4' isomer,
13.2% of the 2,2' isomer,
7.5% of the 3,4' isomer, and
4.5% of the 2,3' isomer.

Neither mono nor trinitro compounds are detected.

375 g of product recovered above are loaded into an autoclave of 5 liter capacity and are placed in suspension in 3.5 liters of methanol. 3.5 g of palladium catalyst deposited at 5% on charcoal are added and the autoclave insulated after having flushed with nitrogen. 40 bars of hydrogen are introduced and the autoclave heated to 100°–120° C. for 1 hour. After cooling, the mixture is recovered, filtered, and the methanol is evaporated. 288 g of the mixture of diphenylethane diamines are collected. The remainder of the nitro derivatives is hydrogenated in the same manner.

Phosgenation then takes place in the following manner: into a reactor of 6-liter capacity there is introduced 3.6 liters of orthodichlorobenzene which is cooled to 5° C. 1.07 kg of liquid phosgene is then run in and 503 g of the mixture of diamines introduced. A precipitate of carbamoyl chloride is formed. Reaction is allowed to take place for 2 hours at ambient temperature, 1 hour at 45° C., 2 hours at 60° C. and one-half hour at 100° C. At that temperature the mixture becomes clear. The mixture is heated to 140° C. and then flushed with nitrogen until total elimination of the phosgene. After cooling, filtration takes place and then the solvent is evaporated. The residue of 614 g constituted of isocyanate isomers is distilled under reduced pressure of 266 Pa. in an apparatus formed by a balloon flask, heated between 230° and 260° C., topped by a distillation bridge. The purified mixture of diisocyanates contains 2 equivalents of NCO per mole and presents itself in the form of a liquid which solidifies at the end of several hours. The mixture then possesses a complete melting point of 50° C. and remains several hours in the liquid state which makes it easy to handle.

Its composition is appreciably the following:
2,4' isomer: 45.0%
4,4' isomer: 30.3%
2,2' isomer: 15.0%
3.4' isomer: 5.0%
2,3' isomer: 4.7%

EXAMPLE 2

18.2 g of diphenylethane are nitrated by operating as in Example 1, but by utilizing 16.6 g of 98.7% nitric acid (30% excess) and 26.5 g of 96% sulfuric acid (30% excess). At the end of the reaction, after distillation of the methylene chloride, there is recovered 25 g of a mixture of nitro derivatives containing 10.9% of trinitro-diphenylethanes leading after hydrogenation and phosgenation, by excluding the triisocyanates formed, to a mixture of diisocyanates of a composition approximately:
2,4' isomer: 38%
4,4' isomer: 40%
2,2' isomer: 11%
3,4' isomer: 7%
2,3' isomer: 4%

EXAMPLE 3

18.2 g of diphenylethane are nitrated by operating as in Example 1, but by utilizing 15.4 g of 90% nitric acid (10% excess) and 25.5 g of 90% sulfuric acid (30% excess). At the end of the reaction, 24.5 g of a mixture of nitro derivatives are obtained containing 8.7% of mononitrodiphenylethanes and after hydrogenation and phosgenation, by excluding the monoisocyanates formed, leading to a mixture of diisocyanates of a composition approximately:
2.4' isomer: 42%
4,4' isomer: 34%
2,2' isomer: 13%
3,4' isomer: 7%
2,3' isomer: 4%

EXAMPLE 4

(COMPARATIVE EXAMPLE)

Oxidizing duplication of the paranitrotoluene in 4,4'-dinitro dibenzyl is carried out according to the description made by H. A. STANSBURY, JR. and W. A. PROOPS in the J. Org. Chem. Vol. 26, p. 4162 (1961). In order to do this, there is placed into a reactor cooled to 5° C. and equipped with an efficient agitation mechanism, 93 g of a 28% solution of methanolic potassium hydroxide. A stream of oxygen is allowed to pass and 27.4 g of paranitrotoluene dissolved in 60 g of ethylene diamine at 99% is slowly introduced by controlling the temperature below 10° C. The reaction is carried out for 1 hour, then diluted with 160 ml of water, filtered and the precipitate washed with water and with methanol. After drying there is recovered 26 g of 4,4'-dinitro dibenzyl containing traces of 4,4'-dinitro stilbene (degree of conversion: 95%).

10 g of this product is hydrogenated in an autoclave of 300 ml capacity by operating in 100 ml of methanol in the presence of 0.2 g of palladium catalyst on charcoal at 5%. The autoclave is raised to 120° C. under 30 bars of hydrogen until a pressure drop is no longer detected. After cooling, filtration of the catalyst, and evaporation of the solvent 7.7 g of 4,4'-diamino diphenylethane of 98–99% purity, are recovered having a melting point of 137° C.

Phosgenation is carried out according to the operating method described in Example 1. After distillation under reduced pressure, one recovers the diphenylethane 4,4'-diisocyanate containing 2 equivalents of NCO per mole and having a melting point of 88°–89° C.

EXAMPLE 5

(COMPARATIVE EXAMPLE)

Oxidizing duplication of 13.7 g of orthonitrotoluene to 2,2'-dinitro diphenylethane is carried out according to the technique described in Example 4. One recovers 6.8 g of the dinitro derivative (degree of conversion: 50%). The hydrogenation of 10 g of the dinitro derivative is carried out as in Example 4 and leads to 7.8 g of 2,2'-diamino dibenzyl melting at 76° C. The phosgenation of the diamine according to the operating method described in Example 1 furnishes the diphenylethane-2,2'-diisocyanate which, distilled, contains 2 equivalents of NCO per mole and has a melting point of 78°–79° C.

EXAMPLE 6

(COMPARATIVE EXAMPLE)

An oxidizing duplication reaction is carried out on a mixture of 18 g of orthonitrotoluene and of 10 g of paranitrotoluene, by operating according to the technique described in Example 4. There is thus recovered 10 g of a solid orangish product formed of the 4,4', 2,2', and 2,4' isomers of dinitrodiphenylethane. After hydrogenation of 9.5 g of the mixture and phosgenation under the conditions described in the preceding examples; after distillation of the solvent, one collects 7.2 g of solid brown isocyanate melting at 60° C., containing 1.90 equivalent NCO/mole and whose distribution of isomers is the following one:
74.7% of 4,4' isomer,
21.3% of 2,2' isomer,
4.0% of 2,4' isomer.

EXAMPLE 7

At 50° C., there is placed into a reactor 100 parts of butanediol polyadipate, 20 parts of butanediol and 3 to 4 drops of tertiary diamine (sold commercially under the name DABCO). At 50° C., a mixture of diphenylethane diisocyanates prepared in Example 1 is allowed to run in in such a way as to have a ratio of NCO/OH=1. Agitation is carried out for 15 seconds and the reaction mixture run into a mold which is placed for 5 hours at 110° C. A semi-rigid plate is then obtained on which the following measurements were carried out:
the Shore hardness D amounts to 30
tensile tests (with a tensile speed of 50 mm/min):
breaking strength (MPA): 23.4
corresponding elongation (%): 672
maximum load (MPa): 25.6
corresponding elongation (%): 668

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A low melting point composition comprising a mixture of diisocyanate isomers having the diphenylethane structure and containing by weight about:
   35 to 55% of the 2,4' isomer,
   15 to 40% of the 4,4' isomer,
   10 to 25% of the 2,2' isomer,
   3 to 10% of the 3,4' isomer, and
   3 to 8% of the 2,3' isomer.

2. The composition of claim 1 consisting essentially of:
   40 to 45% of the 2,4' isomer,
   30 to 40% of the 4,4' isomer,
   10 to 15% of the 2,2' isomer,
   5 to 7% of the 3,4' isomer, and
   4 to 4.5% of the 2,3' isomer.

3. The method of making the composition of claim 1 comprising first nitrating the aromatic rings of diphenylethane with a mixture of at least 90% concentrated nitric acid and at least 90% concentrated sulfuric acid for a time and temperature sufficient to form dinitrated isomers of diphenylethane, hydrogenating the dinitrated isomers at a temperature and for a time sufficient to form to the corresponding diamine isomers, and phosgenating said diamine isomers at a temperature and for a time sufficient to form a composition containing the corresponding diisocyanates.

4. The method of claim 3 wherein the nitric acid is used in amount at least equivalent to one mole thereof per aromatic ring to be nitrated to 20% in excess thereof.

5. Polyurethane formed utilizing a composition of claim 1 or 2.